US009783472B2

(12) United States Patent
Schreck et al.

(10) Patent No.: US 9,783,472 B2
(45) Date of Patent: *Oct. 10, 2017

(54) PROCESS FOR THE CONTINUOUS PRODUCTION OF ETHYLENE GLYCOL FROM CARBOHYDRATES

(71) Applicant: Iowa Corn Promotion Board, Johnston, IA (US)

(72) Inventors: David James Schreck, Lake City, MN (US); Ray Chrisman, Midland, MI (US); Brooke Albin, Charleston, WV (US); Nye Atwood Clinton, Hurricane, WV (US); Marion McKinley Bradford, Hendersonville, NC (US)

(73) Assignee: Iowa Corn Promotion Board, Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,224

(22) Filed: Jun. 22, 2016

(65) Prior Publication Data

US 2016/0304423 A1 Oct. 20, 2016

Related U.S. Application Data

(63) Continuation of application No. 14/715,089, filed on May 18, 2015, now Pat. No. 9,399,610.

(60) Provisional application No. 62/000,087, filed on May 19, 2014.

(51) Int. Cl.
*C07C 45/00* (2006.01)
*C07C 29/00* (2006.01)
*C07C 29/141* (2006.01)
*B01J 23/889* (2006.01)
*C07C 29/145* (2006.01)
*C07C 45/67* (2006.01)
*B01J 23/30* (2006.01)
*B01J 21/02* (2006.01)
*B01J 21/06* (2006.01)
*B01J 23/89* (2006.01)

(52) U.S. Cl.
CPC ............ *C07C 29/141* (2013.01); *B01J 21/02* (2013.01); *B01J 21/066* (2013.01); *B01J 23/30* (2013.01); *B01J 23/8896* (2013.01); *B01J 23/892* (2013.01); *C07C 29/145* (2013.01); *C07C 45/673* (2013.01); *Y02P 20/52* (2015.11); *Y02P 30/20* (2015.11)

(58) Field of Classification Search
CPC .............................. C07C 45/673; C07C 29/141
USPC ................................................ 568/861, 863
See application file for complete search history.

(56) References Cited

U.S. PATENT DOCUMENTS

| 4,317,946 | A  | * | 3/1982  | Costa ................... C07C 29/141 568/862 |
| 6,982,328 | B2 | * | 1/2006  | Werpy ..................... C07C 29/00 536/102 |
| 6,998,504 | B1 |   | 2/2006  | Unverricht et al. |
| 7,619,214 | B2 |   | 11/2009 | Miller et al. |
| 7,652,131 | B2 | * | 1/2010  | Werpy ..................... C07C 29/00 536/102 |
| 7,960,594 | B2 | * | 6/2011  | Zhang ...................... B01J 21/18 568/861 |
| 8,222,464 | B2 |   | 7/2012  | Kalnes et al. |
| 8,323,937 | B2 |   | 12/2012 | Zhang et al. |
| 8,324,433 | B2 | * | 12/2012 | Zhang .................. C07C 29/132 568/861 |
| 8,338,326 | B2 | * | 12/2012 | Zhang ...................... B01J 21/18 502/177 |
| 8,410,319 | B2 | * | 4/2013  | Kalnes ................. C07C 29/132 568/861 |
| 8,692,032 | B2 | * | 4/2014  | Zhang ...................... B01J 21/18 568/861 |
| 8,889,585 | B2 |   | 11/2014 | Zhang et al. |
| 2011/0137085 | A1 |   | 6/2011  | Trahanovsky et al. |
| 2011/0312487 | A1 |   | 12/2011 | Chen et al. |
| 2012/0172633 | A1 |   | 7/2012  | Zhang et al. |
| 2012/0178974 | A1 |   | 7/2012  | Zhang et al. |

(Continued)

FOREIGN PATENT DOCUMENTS

AU 2012238196 B2 10/2012
EP 0319116 6/1989

(Continued)

OTHER PUBLICATIONS

Ji et al. Catalytic conversion of cellulose into ethylene glycol over supported carbide catalysts. Catalysis Today, vol. 147, 2009, 77-85.*
Zhao et al. Catalytic Conversion of Concentrated Glucose to Ethylene Glycol with Semicontinuous Reaction System. Industrial & Engineering Chemistry Research, vol. 52, 2013, 9566-9572.*
Barton, David G et al, "Solid acid catalysts based on supported tungsten oxides", "Topics in Catalysis", 1998, pp. 87-99, vol. 6, Publisher: Department of Chemical Engineering.

(Continued)

*Primary Examiner* — Sikarl Witherspoon
(74) *Attorney, Agent, or Firm* — Davis, Brown, Koehn, Shors & Roberts, P.C.; Kent A. Herink

(57) ABSTRACT

A continuous process for converting carbohydrates to ethylene and propylene glycol. The carbohydrates are mixed with water and passed through a reactor at a temperature that hydrolyzes the carbohydrate mixture at least partially to monosaccharides. The reactor has a first zone comprising a retro-aldol catalyst and a second zone comprising a reducing catalyst. The aldose is converted in the first zone into glycolaldehyde by the retro-aldol catalyst and the glycolaldehyde, in the presence of hydrogen, is converted to ethylene glycol in the second zone of the reactor. The reaction products are removed from the reactor and the ethylene glycol is recovered. The selectivity to propylene glycol can be enhanced via feeding ketose as the carbohydrate.

20 Claims, 1 Drawing Sheet

(56) References Cited

U.S. PATENT DOCUMENTS

| | | |
|---|---|---|
| 2012/0323051 A1 | 12/2012 | Powell |
| 2013/0281733 A1 | 10/2013 | Han et al. |
| 2014/0039224 A1 | 2/2014 | Adlaf et al. |
| 2016/0207856 A1 | 7/2016 | Can Der Heide et al. |

FOREIGN PATENT DOCUMENTS

| | | |
|---|---|---|
| JP | H01-168345 A | 7/1989 |
| JP | 2002539102 | 11/2002 |
| JP | 2011219447 | 4/2011 |
| WO | 2010119351 A1 | 10/2010 |
| WO | 2012125276 A2 | 9/2012 |
| WO | 14161852 A1 | 10/2014 |
| WO | 14173973 A1 | 10/2014 |
| WO | 2016114659 | 7/2016 |
| WO | 2016114660 | 7/2016 |
| WO | 2016114661 | 7/2016 |

OTHER PUBLICATIONS

Osmundsen, "Catalytic Conversion of Carbohydrates", "Department of Physics", Feb. 2013, Publisher: Technical University of Denmark.

Ji, Na et al, "Catalytic Conversion of Cellulose into Ethylene Glycol Over Supported Carbide Catalysts", "Catalysis Today", 2009, pp. 77-85, vol. 147, Publisher: Science Direct.

Jing Qi et al, "Kinetics of Non-catalyzed Decomposition of Glucose in High-temperature Liquid Water", "Chinese Journal of Chemical Engineering", 2008, pp. 890-894, vol. 16, No. 6, Publisher: Department of Chemical and Biochemical Engineering, Zhejiang University, Hangzhou.

Ooms, Roselinde et al, "Conversion of sugars to ethylene glycol with nickel tungsten carbide in a fed-batch reactor: high productivity and reaction network elucidation", "Green Chemistry", 2014, pp. 695-707, vol. 16, Publisher: The Royal Society of Chemistry.

Jifeng Pang et al, "Catalytic conversion of cellulosic biomass to ethylene glycol: Effects of inorganic impurities in biomass", "Bioresource Technology", 2014, pp. 424-429, vol. 175, Publisher: Elsevier Ltd.

Pang, Jifeng et al, "Catalytic Hydrogenation of Corn Stalk to Ethylene Glycol and 1,2-Propylene Glycol", "Industrial and Engineering Chemistry Research", 2011, pp. 6601-6608, vol. 50, Publisher: ACS Publications.

Ross-Medgaarden et al, "New insights into the nature of the acidic catalytic active sites present in ZrO2-supported tungsten oxide catalysts", "Journal of Catalysis", 2008, pp. 108-125, vol. 256, Publisher: Science Direct.

Sun, Ruiyan et al, "Versatile NickelLanthanum(III) Catalyst for Direct Conversion of Cellulose to Glycols", "American Chemical Society", 2015, pp. 874-883, vol. 5, Publisher: ACS Catalysis.

Zhijun Tai et al, "Temperature-controlled Phase-transfer Catalysis for Ethylene Glycol Production from Cellulose", "Electronic Supplementary Material (ESI) for Chemical Communications", 2012, pp. 1-12, Publisher: The Royal Society of Chemistry.

Aiqin Wang et al, "One-Pot Conversion of Cellulose to Ethylene Glycol with Multifunctional Tungsten-Based Catalysts", "Accounts of Chemical Research", 2013, pp. 1377-1386, vol. 46, No. 7.

You, Su Jin et al, "Direct Conversion of Cellulose into Polyols over Pt/CsxH3-xPW12O40", "Clean Technology", Mar. 2013, pp. 13-21, vol. 19, No. 1, Publisher: Division of Energy Systems Research and Department of Cheical Engineering.

Guanhong Zhao et al, "Catalytic Conversion of Concentrated Glucose to Ethylene Glycol with Semicontinuous Reaction System", "Industrial and Engineering Chemistry Research", 2013, pp. 9566-9572, vol. 52, Publisher: ACS Publications.

Ming-Yuan Zheng et al, "Transition MetalTungsten Bimetallic Catalysts for the Conversion of Cellulose into Ethylene Glycol", "ChemSusChem", 2010, pp. 63-66, vol. 3, Publisher: InterScience.

Deng, Tianyin et al., "Promoting effect of SnOx on selective conversion of cellulose to polyols over bimetallic Pt-SnOx/Al2O3 catalyst", "Green Chemistry", 2013, pp. 116-124, vol. 15, Published in: U.K.

\* cited by examiner

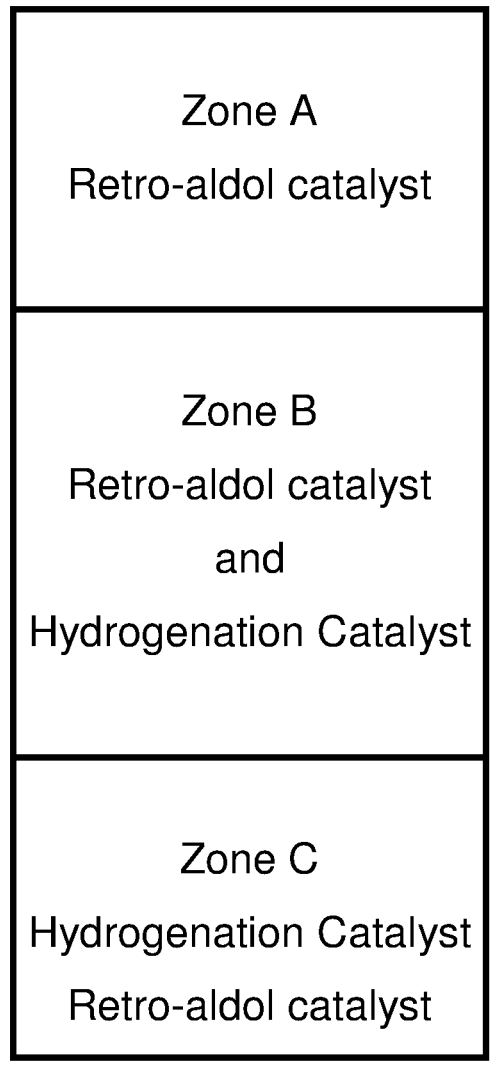

PROCESS FOR THE CONTINUOUS PRODUCTION OF ETHYLENE GLYCOL FROM CARBOHYDRATES

This application is a continuation of U.S. patent application Ser. No. 14/715,089, filed May 18, 2015, which claims priority to U.S. Patent Application Ser. No. 62/000,087, filed May 19, 2014, and incorporates the same herein in their entirety by this reference.

BACKGROUND OF THE INVENTION

This invention relates generally to a process for the production of glycols and, more specifically, to a catalyzed continuous process to convert carbohydrates to mainly either ethylene glycol or propylene glycol.

Ethylene glycol is a valuable commodity chemical that has a broad range of uses as both a building block for other materials such as polyethylene terephthalate (PET) and for its intrinsic properties such as for antifreeze. It is currently made by a multistep process that starts with ethylene derived from hydrocarbon feedstocks.

A cost-effective way to produce ethylene glycol from renewable resources would reduce dependence on non-renewable hydrocarbon feedstocks and create substantial new uses for agricultural based products. Several patents have demonstrated that carbohydrates, one of the most abundant renewable resources, can be converted to ethylene glycol.

Early approaches have been based on the use of somewhat non-selective hydrogenolysis for the conversion of carbohydrates to ethylene glycol. As an example U.S. Pat. No. 5,210,335 describes a reaction system with a high catalyst loading that produces 20 wt. % ethylene glycol and 60 wt. % propylene glycol plus a range of other components. EP2419393 "Method for the hydrogenolysis of sugar alcohols" has reduced the required catalyst concentration, but still produces a range of products with ethylene glycol being only about 8-12 mole % of the final product. These approaches will require extensive post reactor separations and markets for the various co-products to be cost effective.

Recent work described in U.S. Pat. Appl. 2012/0172633 (Zhang, et al.) using a low catalyst loading has demonstrated a much higher selectivity to ethylene glycol by achieving a yield of greater than 50% to as high as 68% depending on the choice of feedstocks. However, the reactor concentrations demonstrated were not commercially viable at only 1% solution of the feedstock. A very recent paper has demonstrated that the reason for the higher selectivity is due to a different mechanism for tungsten based catalysts (Ooms, R., et al. Conversion of sugars to ethylene glycol with nickel tungsten carbide in a fed-batch reactor: high productivity and reaction network elucidation. *Green Chem.*, 2014, 16, 695-707). Initially the tungsten very selectively converts aldohexoses such as glucose to glycolaldehyde and erythrose by a retro-aldol mechanism and then further converts the erythrose into two more glycolaldehydes. The glycolaldehydes are hydrogenated by another catalyst to the ethylene glycol. The problem in the Zhang application and the Ooms paper is that the writers try to do the whole reaction sequence in one process step which introduces unnecessary complexity to the catalyst composition and manufacturing process and as importantly generates more impurities.

In addition, all of the methods described above are batch or semi-batch which are not as cost-effective for commodity production processes. In addition the described methods operate in stirred reactors with very high agitation rates, which rapidly powders the solid catalyst particles. Powdered reduction catalysts can be a very major operating hazard in commercial scale production processes. This invention improves the selectivity to the desired glycol product, increases the processing concentrations to more commercially viable levels and demonstrates a safer, continuous process for the cost-effective production of glycols from carbohydrates.

SUMMARY OF THE INVENTION

The process of the present invention takes place in two areas, a catalysis area and a recovery area. The catalysis area comprises a feed tank wherein a bio-sourced carbohydrate feedstock is mixed with solvent to adjust the concentration of starting carbohydrate to approximately 5 to 71 wt % carbohydrates in solvent. The preferred carbohydrate feedstock for the process is a carbohydrate polymer such as starch, cellulose, or partially hydrolyzed fractions of such polymers or mixtures of the polymers or mixtures of the polymers with partially hydrolyzed fractions; glucose or, if higher levels of propylene glycol are desired, fructose can be utilized as the feedstock.

The carbohydrate mixture in the solvent is fed into a reactor where it sequentially contacts initially a retro-aldol catalyst and secondly a reducing catalyst. Hydrogen is fed either at the beginning of the catalyst reactor or at an alternate point to the reactor. Product is removed at the outlet of the reactor and processed for recovery of the product, glycol.

For the production of ethylene glycol the catalyst reactor used contains several catalysts chosen to have different properties in order to conduct different chemical conversions. At the first portion of the catalytic reactor, the catalyst is comprised of a retro-aldol catalyst that catalyzes the conversion of glucose to glycolaldehyde and erythrose. This same catalyst will also catalyze the reaction of erythrose to two additional moles of glycolaldehyde. If a carbohydrate mixture containing carbohydrates larger than a monosaccharide is used as the carbohydrate feedstock, in the presence of water, it will partially hydrolyze and eventually become glucose molecules as it travels through the catalyst reactor. Part of the way through the reactor, a second catalyst is encountered as a distinct second catalyst phase. This second catalyst is chosen for its ability to reduce the glycolaldehyde to ethylene glycol using the hydrogen fed to the reactor. As the feedstock moves through the reactor, from beginning to end, the amount of reducing catalyst increases as a fraction of the amount of catalyst encountered in the reactor.

An object of the present invention is to provide a process for the continuous production of ethylene glycol from a carbohydrate feedstock, and preferably a bio-sourced carbohydrate feedstock in which the carbohydrate concentration of the feedstock is between 5% and 71%.

Another object of the present invention is to provide a process for the continuous production of ethylene glycol with a selectivity to ethylene glycol of up to at least 59%.

A further object of the present invention is to provide a process for the continuous production of ethylene glycol which results in a product having up to at least 4.9% organic concentration.

Yet another object of the present invention is to provide a process for the continuous production of propylene glycol from a carbohydrate feedstock, and preferably a bio-sourced carbohydrate feedstock, with a selectivity to propylene glycol of up to at least 24%.

A still further object of the invention to add at least a portion of the reduction catalyst to the carbohydrate feedstock.

BRIEF DESCRIPTION OF THE DRAWINGS

FIG. 1 is a schematic diagram of a reactor for use in the present invention.

DETAILED DESCRIPTION OF THE INVENTION

As used herein, the term "aldose" refers to a monosaccharide that contains only a single aldehyde group (—CH=O) per molecule and having the generic chemical formula $C_n(H2O)_n$. Non-limiting examples of aldoses include aldohexose (all six-carbon, aldehyde-containing sugars, including glucose, mannose and galactose), aldopentose (all five-carbon aldehyde containing sugars, including xylose and arabinose), aldotetrose (all four-carbon, aldehyde containing sugars, including erythrose), and aldotriose (all three-carbon aldehyde containing sugars, including glyceraldehyde).

As used herein, the term "bio-sourced carbohydrate feedstock" refers to a product that includes carbohydrates sourced, derived or synthesized from, in whole or in significant part, biological products or renewable agricultural materials (including, but not limited to, plant, animal and marine materials) or forestry materials.

As used herein, the term "ketose" refers to monosaccharides containing one ketone group (=O) per molecule. Non-limiting examples of ketoses include ketohexose (all six-carbon, ketone-containing sugars, including fructose), ketopentose (all five-carbon ketone containing sugars, including xylulose and ribulose), ketotetrose (all four-carbon, ketone containing sugars, including erythrulose), and ketotriose (all three-carbon ketose containing sugars, including dihydroxyacetone).

As used herein, the term "reducing metal catalyst" refers to catalysts that assist in the reduction of carbonyls. Nickel, palladium and platinum are among the more widely used reducing metal catalysts. Nickel-rhenium is a preferred reducing metal catalyst and may be supported on alumina-silica. Nickel-iridium may also be used. We have also found Ni—Re catalysts with B as a promoter is very good in this application.

As used herein, the term "retro-aldol catalyst" refers to a catalyst that catalyzes the retro-aldol reaction. Retro-aldol catalysts preferred in practicing the present invention include tungsten and its oxides, sulfates, phosphides, nitrides, carbides, halides and the like that convert to a form of a catalytically active hydrated tungsten species supported on a carrier. Tungsten carbide and soluble phosphotungstens are also included. Tungsten oxides supported on zirconia, alumina and alumina-silica. Soluble tungsten compounds, such as ammonium metatungstate, have been found to be an acceptable precursor to an active retro-aldol catalyst. Other forms of soluble tungstates, such as ammonium paratungstate and sodium metatungstate, are also included.

In preferred embodiments of the present invention, the starting composition of the carbohydrate feedstock is between 5% and 71% carbohydrate and all values between such limits, including, for example, without limitation or exception, 6%, 13.43%, 31.5%, 31.55%, 44%, 51.01%, 63.33% and 69.9%. Stated another way, in preferred embodiments of the invention, the carbohydrate concentration of the feedstock can take any value "ab.cd" % wherein a is selected from the numerals 0, 1, 2, 3, 4, 5, 6 and 7, and b, c and d are each individually selected from the numerals 0, 1, 2, 3, 4, 5, 6, 7, 8 and 9, with the exception that b cannot be less than 5 if a is 0 nor can b be greater than 1 if a is 7.

Where ranges are used in this disclosure, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3. 6.3, 0.815 and so forth) are included as are all intermediate ranges (e.g., 0.2-0.5, 0.54-0.913, and so forth)

The process comprises two areas—the catalysis area and the recovery area. The catalysis area comprises a feed tank wherein the bio-sourced feed is mixed with solvent to adjust the concentration of starting carbohydrate to approximately 5 to 71 wt % carbohydrates in solvent. However even higher concentrations, if available, can be used if the feed rate is matched to the process reaction rates. In order for the hydrolysis of the carbohydrate which is larger than a monosaccharide into glucose, water is required to be at least a portion of the solvent used in the process. Among the more desirable additional components in the solvent is ethylene glycol and it can be obtained from the reactor outlet product which is a mixture of the reaction products which can also include recycled retro-aldol catalyst. This means that it is possible that a portion of the crude reactor outlet can be recycled and used as solvent for the reaction.

The preferred carbohydrate feedstock for the process is a carbohydrate polymer such as starch, cellulose, or partially hydrolyzed fractions of such polymers or mixtures of the polymers or mixtures of the polymers with partially hydrolyzed fractions. One of the desired hydrolyzed fractions consists of glucose. Thus it is acceptable to have glucose or glucose precursors as a portion of the reactor feed. It is also acceptable to have glucose as a major portion or sole reactive component of the reactor feedstock.

Other aldoses, sugars with an aldehyde group, can also be used. Carbohydrates that produce ketoses, such as fructose, will increase the selectivity to propylene glycol by this sequence of catalysts.

In the process, the carbohydrate mixture in the water miscible solvent is fed into a reactor where it sequentially contacts initially a retro-aldol catalyst and secondly a reducing catalyst. In the process, the carbohydrate mixture is fed at the beginning of a catalyst reactor and hydrogen is fed either at the beginning of the reactor or at an alternate point to the reactor. Product is removed at the outlet of the reactor and processed for recovery of the product, glycol, or for partial recycle to the reactor. Various types of catalyst bed designs can be employed, among which a trickle bed or bubble column is favored, to aid in the diffusion of hydrogen to the reducing catalyst surface.

In one embodiment, which is useful with soluble retro-aldol catalysts, the reactor can be a CSTR in which a solid phase reducing catalyst is suspended in, but it does not occupy the full volume, of the reactor. This arrangement protects the solid catalyst from mechanical breakdown due to the agitator. This design also provides a solid phase supported-catalyst free zone where the initial retro-aldol reaction can be catalyzed free of the solid-phase reducing catalyst and the retro-aldol reaction products are subsequently reduced by the solid phase catalyst. The presence of a zone that is free of reducing catalyst allows the retro aldol reaction to proceed and lowers the amount of glucose that is reduced to sorbitol in the reaction. Sorbitol is an unwanted by-product of the reaction.

The catalyst reactor used contains several catalysts chosen to have different properties in order to conduct different chemical conversions. At the first catalytic portion of the reactor—the retro-aldol zone—the catalyst is comprised of a retro-aldol catalyst that if glucose is the starting material catalyzes the conversion of glucose to glycolaldehyde and erythrose. This same catalyst will also catalyze the reaction of erythrose to two additional moles of glycolaldehyde. If starch or similar carbohydrates is used, due to the temperatures employed the carbohydrate polymer mixture, in the presence of water, while being fed to the reactor, partially hydrolyzes and eventually becomes glucose molecules as it enters the reactor and travels through the catalyst reactor. Part of the way through the reactor a second catalyst is encountered as a distinct second catalyst or it is mixed in with the retro-aldol catalyst. This second catalyst has been chosen for its ability to reduce the glycolaldehyde to ethylene glycol using the hydrogen fed to the reactor. As the carbohydrate reactant moves through the reactor, from beginning to end, the amount of reducing catalyst increases as a fraction of the amount of catalyst encountered in the reactor. At the end of the catalyst bed the amount of reducing catalyst can be nearly 100% of the catalyst in this portion of the bed if the retro-aldol catalyst is supported. It is possible for the two reactions to be done in two or more reactors.

In the accompanying schematic of the reactor (FIG. 1) it is shown that the first zone (identified as Zone A) is mostly retro-aldol catalyst. The function of this catalyst zone as mentioned previously is to cause the glucose to produce glycolaldehyde and erythrose. The same catalyst can also decompose erythrose selectively to two moles of glycolaldehyde. It is necessary to reduce the formed glycolaldehyde to ethylene glycol which is the desired product. For this reason the reducing catalyst is present in the reactor. However it may not be practical to wait until all the glucose has been decomposed before beginning to reduce the glycolaldehyde. For this reason, part of the way down the reactor, the reducing catalyst can be mixed with the retro-aldol catalyst and some of the glycolaldehyde will be converted to ethylene glycol but still allowing un-reacted glucose and erythrose to be converted to glycolaldehyde. In the case where the two catalysts are mixed, this is identified as Zone B. As the carbohydrate is consumed and glycolaldehyde formation drops the need for the retro-aldol catalyst drops and the percentage of reducing catalyst in the reducing zone of the bed increases until near the bottom of the reactor the reducing catalyst comprises a large proportion of the catalyst (identified as Zone C). It is not required that Zone C be used but it can lead to higher overall selectivity to ethylene glycol. If the reducing catalyst is a solid it is acceptable to dilute the active supported catalyst with inert materials such as the support used for the catalyst or possibly glass beads or the like.

The catalysis zones of the process operate at high temperatures. The initial zone of the bed operates from 170 to 300° C., more preferably in the range of 190 to 270° C., and most preferably in the range of 190 to 255° C. The lower section of the bed can operate at lower temperatures, between 90 to 245° C., with the preferred range for the reaction being between 150 to 245° C. The bed temperature can be controlled via addition of additional, cooler solvent at various feed points along the reactor bed or the use of an inter-stage cooler. However with close-coupled zones it is most likely that the zones will be at comparable temperatures It is possible to physically separate the catalyst zones into separate reactors for improved control of bed temperatures and system pressures. Such optimization is more costly from an investment perspective and the trade-offs between investment and return on investment will change as the cost of the feedstock changes.

The reactor pressure can be operated from 300 to 2000 psig. The preferred range is such that it will ensure that hydrogen is dissolved into the solvent phase and is replenished from the vapor phase as it is consumed in the reducing reaction. The use of a trickle bed or bubble column is preferred to provide mixing of the hydrogen into the liquid phase and to directly replenish the hydrogen depleted from the catalyst surface when the gas bubbles directly contact the catalyst surface. The preferred range is 400-1600 psig.

The amount of catalyst required in the packed bed is dependent on the flow-rate of carbohydrate to the reactor. The higher the feed rate, the larger the amount of catalyst required to provide high conversion of the carbohydrate.

The carbohydrate mixture that is used as the reactor feed can be pre-heated prior to its introduction into the reactor. This heating in an aqueous environment allows depolymerization of the starch or cellulose polymers into lower molecular weight oligomers and the production of glucose or other 4 to 6 carbon aldoses prior to introduction into the reactor. The carbohydrate can also be hydrolyzed to form glucose or other 4 to 6 carbon aldoses by other means prior to introduction into the reactor such as by acids or enzymes or combinations of both.

The carbohydrate feed can be mostly fructose or carbohydrates that will yield ketoses. If this is the starting material and the same reaction sequence is followed then the majority of the product will be propylene glycol.

The carbohydrate feed may also be a one which will yield aldoses and ketoses, such as sucrose. If this is the starting material and the same reaction sequence is followed then the product will be a ratio of ethylene glycol and propylene glycol, dependent on the aldose to ketose ratio.

The retro-aldol catalyst zone, designated Zone A utilizes a retro-aldol catalyst that can be a form of tungsten or its oxides, sulfates, phosphides, nitrides, carbides, halides and the like that convert to some form of catalytically active tungsten species supported on a carrier. In related prior art tungsten carbide has been used as well as soluble phosphotungstates. In addition to the use of these forms of tungsten, tungsten oxides supported on zirconia, alumina or alumina silica can be used as the source of the retro-aldol catalyst. In the present work soluble tungsten compounds such as ammonium metatungstate have been found to be an acceptable precursor to an active retro-aldol catalyst. We have also shown in our work that other forms of soluble tungstates work well—among them are ammonium paratungstate and sodium metatungstate.

Without wishing to be limited to known retro-aldol catalysts the concept is simply to use selective retro-aldol catalysts in Zone A. Although the specific ones mentioned appear to be acidic or neutral in nature it is possible that basic retro-aldol catalysts will be discovered that will also function well in this reactor design.

The reducing catalyst can be chosen from a wide variety of supported transition metal catalysts. Nickel and ruthenium as the primary reducing metal components are well known for their ability to reduce carbonyls. One particularly favored catalyst for the reducing catalyst in this process is a Ni—Re catalyst supported on alumina silica. A similar version of Ni/Re or Ni/Ir can be used with good selectivity for the conversion of the formed glycolaldehyde to ethylene glycol.

The mid-portion of the catalytic reactor is designated Zone B when a mixture of catalysts is used and in this zone both retro-aldol and reducing catalysts are found. The purpose is to begin the conversion of the intermediate formed glycolaldehyde to ethylene glycol before its concentration becomes so high that significant by-product formation begins from reactions of the glycolaldehyde with itself or other intermediates. When the catalytic bed is built if a Zone B is to be used it is helpful that Zone B is well-mixed with both catalysts. If the retro-aldol catalyst is not supported then Zone B will be the area where the retro-aldol catalyst begins being mixed with the reducing catalyst.

Maintaining the solid catalysts in a bed or basket type format away from any agitator increases the mechanical lifetime of the catalysts. Mechanical stability of the catalyst greatly improves process safety and reduces the potential for actuator failure due to particle problems. Powdered reduced metals such as Ni, Fe and the like are responsible for many serious industrial incidents since when they are exposed to oxygen in the air when maintenance is performed fires result.

In one preferred option the reactor chosen is a CSTR that contains a porous catalyst "basket" that is suspended in the reactor. Examples of such catalyst baskets for stirred reactors are available from Parr Instrument Company. The basket contains solid catalyst and occupies approximately 2% of the liquid volume of the reactor. Containment of the solid reduction catalyst also improves the handling ease and process safety when using reduction catalyst particles. When the reaction is run the liquid portion of the reactor that is outside of the basket is approximately 98% of the reactor liquid and is referred to as Zone A. The 2% of the reactor liquid volume in the basket is referred to as Zone B. Example 5 is a description of the operation and provides good evidence that separation of the solid reduction catalyst from a significant portion of the soluble retro-aldol portion of the reactor allows each reaction to proceed independently and provide high selectivity to ethylene glycol. In this operation the raw material is added to the reactor in such a way that the feed initially contacts the basket-free Zone A allowing the retro-aldol reaction to dominate before the products of the reaction contact Zone B.

In a second preferred option the reactor chosen is a tubular reactor that contains the supported Ni—Re reduction catalyst. There is a portion of this reactor that is free of reducing catalyst where the feedstock and the soluble retro-aldol catalyst are contacted at the reaction temperature of approximately 245 C. This is the Zone A referred to earlier in this application. Downstream of Zone A the reaction stream contacts the supported reducing catalyst where both the reduction of the glycolaldehyde and further retro-aldol reactions are occurring due to the presence of some unreacted glucose and erythrose with the retro-aldol catalyst. Hydrogen is fed to the tubular reactor to allow the reduction of the glycolaldehyde to ethylene glycol.

Although the catalyst bed may be loaded with supported catalysts this in no means suggests that it is not possible or undesirable to also employ soluble retro-aldol or reducing catalysts. As is suggested in relevant art, soluble forms of tungsten such as phosphotungstic acid are capable of conducting the retro-aldol reaction and its use or the use of similar soluble retro-aldol catalysts are compatible with the zoned catalyst bed concept. As already mentioned, it may be inferred from this application that a separate reactor used just with the retro-aldol catalyst could be used to generate glycolaldehyde which could then be fed to the reducing catalyst reactor. However it is likely that conducting the two reactions—retro-aldol and reduction—separately will increase investment.

What is important to good performance in this process for producing glycols is that the reducing portion of the reaction sequence be separated initially, in part, from the retro-aldol portion of the reaction. Since this is a sequential reaction the initial reaction should be the retro-aldol, followed by both retro-aldol and reduction and finally mainly reduction to convert the remaining glycolaldehyde to ethylene glycol. Having retro-aldol catalyst present with the reducing catalyst is not a problem but lower selectivity will result if the feedstock does not initially encounter the retro-aldol catalyst.

Following the catalytic portion of the process, a part of the product stream may be separated for recycle back to the front of the process. Depending on the mode of separation this recycle stream can contain ethylene glycol and soluble retro-aldol catalyst among other components. The remaining reactor effluent may then be depressurized and cooled to begin the recovery portion. The gases are captured for recovery of the hydrogen and removal of unwanted gaseous by-products such as methane and carbon dioxide.

Upon cooling, less soluble portions of catalysts that were solubilized from the bed or that were fed to the reactor are removed at the reduced temperature and the remaining liquid is transferred to the recovery portion of the process.

In recovery the low boiling components such as ethanol and methanol are removed via distillation. Water is also removed via distillation followed by recovery of propylene glycol and ethylene glycol. It is typical in the manufacture of ethylene glycol to use multi-effected evaporators to minimize energy usage in the recovery of the ethylene glycol.

It is likely that separation of the ethylene glycol from the propylene glycol or other close boiling glycols will require an additional, more sophisticated separation technology. Simulated Moving bed technology is one such option that can be used. The choice is dependent on the quality of the product that is required by the desired end use for the product.

Example 1

In this first example the catalyst reactor which is equipped with a stirrer to provide agitation is charged only with the reducing catalyst and operated at 245° C. The feed consists of glucose at 20 wt % in water and is fed at the top of the reactor. Hydrogen is fed into the reactor at 1500 psig. No retro-aldol catalyst is provided. Once the reactor is lined out samples are collected and the conversion of glucose to ethylene glycol is very low with modest amounts of propylene glycol also formed. The major product formed is sorbitol.

Example 2

In this experiment similar to example 1 the catalyst reactor is charged only with a retro-aldol catalyst and operated at 245° C. The carbohydrate feed composition is the same as that used in Example 1 and is fed at the top of the reactor. Hydrogen is fed at 1500 psig. Once the reactor is lined out samples are collected and analyzed. The conversion to ethylene glycol is low with many unidentified products made.

Example 3

In this experiment similar to example 1 the catalyst reactor is charged with retro-aldol catalyst and reducing catalyst and operated at 245° C. In this configuration the incoming feed encounters both the reducing catalyst and the retro-aldol catalyst as soon as it enters the reactor. The feed composition is the same as that used in Example 1. Hydrogen is fed at 1500 psig. Once the reactor is lined out samples are collected and analyzed. The major product identified is ethylene glycol but substantial amounts of sorbitol are also identified. Higher levels of propylene glycol are also identified.

Example 4

In this experiment similar to example 1 the catalyst reactor is charged with reducing catalyst suspended in a basket in the reactor. In the initial portion of the reactor, where initial contact with the carbohydrate feed occurs, only the soluble retro-aldol catalyst is present. The carbohydrate feed composition is the same as that used in Example 1 and is fed at the top of the reactor. Hydrogen is fed at 1500 psig. Once the reactor is lined out samples are collected and analyzed. The major product found is ethylene glycol with low levels of propylene glycol. The amount of sorbitol formed is lower than in Examples 1 and 3.

Example 5

A fed-batch reaction was carried out to react an aqueous glucose solution to ethylene glycol. A 300 ml stainless steel Autoclave Engineers stirred high pressure reactor was charged with 145 ml of deoxygenated distilled water, 0.30 g of ammonium metatungstate and 2.2 grams of Ni/Re/B containing alumina silica catalyst. The previously reduced Ni/Re/B catalyst was carefully transferred under nitrogen atmosphere into a static catalyst basket fixed to the internals of the reactor. The reactor was then sealed and then subjected to three nitrogen purges followed by three hydrogen purges to remove any oxygen from the system. Finally the reactor was pressurized to 650 psi with hydrogen and the contents heated to 245° C. The agitator was operated at 1000 rpm. When the target temperature was reached the pressure was adjusted to 1550 psi with hydrogen and the feeding of 33% glucose in water was initiated. The glucose was injected into the area of the reactor free of the catalyst basket. 25 grams of feed was injected into the reactor at a constant rate over 2 hours. At the end of the feed the reaction was concluded. The final product weighed 170 grams and had a 4.9% cumulative organic concentration. The reactor was cooled rapidly in an ice bath and a sample of the contents was submitted for analysis. The GC analysis indicated 59% selectivity to ethylene glycol with a 15/1 ratio of ethylene glycol to propylene glycol. The sorbitol selectivity was 1.4%.

The yield of each component was calculated using the following equation:

$$\text{Selectivity}(\%) = \frac{\text{weight of component in product}}{\text{Weight of glucose fed to the reactor}} \times 100\%$$

Example 6

An experiment was conducted in which aqueous fructose feed was reacted in the presence of a homogeneous retro-aldol catalyst and a heterogeneous reduction catalyst to produce a mixture of ethylene glycol and propylene glycol. For this experiment, a catalyst basket was used to hold the heterogeneous hydrogenation catalyst so that the two reaction steps would be largely separated into two zones. A 300 ml 316SS stirred high-pressure Autoclave Engineers reactor was charged with 145 g of deoxygenated distilled water, 0.3 g of ammonium metatungstate and 2.1 g of Ni/Re/B containing alumina silica catalyst. The previously reduced Ni/Re/B catalyst was carefully transferred under a nitrogen atmosphere to a static catalyst basket fixed to the internals of the reactor and the catalyst was immediately covered with water. The reactor was sealed and then purged with nitrogen three times and hydrogen three times. Next, the reactor was pressurized to 500 psig with hydrogen and the contents were heated to 245° C. The agitator was operated at 1000 rpm. When the reactor reached its target operating temperature, the pressure was adjusted to 1550 psig with hydrogen. 25 g of 33% fructose in water was fed to the reactor at a constant rate over 2 hours. At the end of the feed the experiment was concluded. The final product weighed 170 g and had a 4.9% cumulative organic concentration. The reactor was cooled rapidly with an ice bath and a sample of the contents was submitted for analysis. The GC analysis identified propylene glycol as the major product. Propylene glycol was produced with 24% selectivity and ethylene glycol was produced with 10% selectivity. The LC analysis indicated that glycerin was generated at approximately 7% selectivity. Only 1.4% sorbitol was detected.

SUMMARY

It is found that use of "sequential" catalysts—where the initial catalyst zone encountered by the feedstocks is largely the retro-aldol catalyst followed by a second zone of catalyst where the retro-aldol catalyst is diluted with a solid reducing catalyst—provides high selectivity to ethylene glycol and a safer more commercially viable mode of operation over catalysis approaches where the two types of catalysts are encountered simultaneously by the reactor feed in a stirrer reactor.

One additional manifestation of this use of sequential catalysts for the conversion of carbohydrates to ethylene glycol is that it is possible for the reducing catalyst to be maintained in a separate reactor which allows for wider latitude in choosing reaction conditions for optimizing the retro-aldol reaction separate from the optimal conditions for the reducing catalyst. Although this option will result in potentially higher investment it may be possible to off-set the higher investment cost with savings from improved selectivity to ethylene glycol.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A continuous process for converting carbohydrates, which can yield at least one of aldoses and ketoses, to a glycol product of at least one of ethylene glycol and propylene glycol by catalytic conversion at elevated temperature using retro-aldol catalyst and reducing catalyst in the presence of hydrogen, comprising the steps of:
   (a) passing a solution of carbohydrates to an initial catalyst zone comprising retro-aldol catalyst and then to at least one sequential catalyst zone comprising reducing catalyst in which the retro-aldol catalyst is diluted with the reducing catalyst;
   (b) withdrawing from which sequential catalyst zone an effluent containing glycol product.

2. The process of claim 1 wherein the retro-aldol catalyst is provided by soluble tungstate.

3. The process of claim 2 wherein the carbohydrate comprises glucose, and ethylene glycol is produced.

4. A continuous process for converting carbohydrates, which can yield at least one of aldoses and ketoses, to a glycol product of at least one of ethylene glycol and propylene glycol by catalytic conversion at elevated temperature using retro-aldol catalyst and reducing catalyst in the presence of hydrogen, comprising at said elevated temperature the steps of:
   (a) passing a solution of carbohydrates of approximately 5 to 71 wt % to an initial catalyst zone comprising retro-aldol catalyst and then to at least one sequential catalyst zone comprising reducing catalyst in which the retro-aldol catalyst is diluted with the reducing catalyst;
   (b) withdrawing from which sequential catalyst zone an effluent containing glycol product.

5. The process of claim 4 wherein the retro-aldol catalyst is provided by soluble tungstate.

6. The process of claim 5 wherein the carbohydrate comprises glucose, and ethylene glycol is produced.

7. A continuous process for converting carbohydrates, which can yield at least one of aldoses and ketoses, to a glycol product of at least one of ethylene glycol and propylene glycol by catalytic conversion at elevated temperature using retro-aldol catalyst and reducing catalyst in the presence of hydrogen, comprising the steps of:
   (a) passing a solution of carbohydrates to an initial catalyst zone comprising retro-aldol catalyst and then to at least one sequential catalyst zone comprising solid reducing catalyst in which the retro-aldol catalyst is diluted with the solid reducing catalyst;
   (b) withdrawing from which sequential catalyst zone an effluent containing glycol product, wherein the initial catalyst zone comprising retro-aldol catalyst produces intermediates that enable selectivity to the glycol product to be increased.

8. The process of claim 7 wherein the retro-aldol catalyst is provided by soluble tungstate.

9. The process of claim 8 wherein the carbohydrate comprises glucose, and retro-aldol catalyst produces intermediates that enable lowering the amount of sorbitol formed.

10. The process of claim 9 wherein ethylene glycol is produced.

11. The process of claim 10 wherein the solution of carbohydrates comprises ethylene glycol.

12. The process of claim 7 wherein a portion of the effluent containing glycol product is recycled as solvent for the carbohydrate solution.

13. A continuous process for converting carbohydrates, which can yield at least one of aldoses and ketoses, to a glycol product of at least one of ethylene glycol and propylene glycol by catalytic conversion at elevated temperature using retro-aldol catalyst and reducing catalyst in the presence of hydrogen, comprising at said elevated temperature the steps of:
   (a) passing a solution of carbohydrates of approximately 5 to 71 wt % to an initial catalyst zone comprising retro-aldol catalyst and then to at least one sequential catalyst zone comprising solid reducing catalyst in which the retro-aldol catalyst is diluted with the solid reducing catalyst;
   (b) withdrawing from which sequential catalyst zone an effluent containing glycol product.

14. The process of claim 13 wherein a preheated zone prior to the catalysis zone hydrolyzes the carbohydrates at least partially to monosaccharides.

15. The process of claim 13 wherein the reduction catalyst is selected from the group consisting of nickel-rhenium (Ni/Re) and nickel-iridium (Ni/Ir).

16. The process of claim 13 wherein the retro-aldol catalyst is provided by soluble tungstate.

17. The process of claim 16 wherein the carbohydrate comprises glucose, and retro-aldol catalyst produces intermediates that enable lowering the amount of sorbitol formed.

18. The process of claim 17 wherein ethylene glycol is produced.

19. The process of claim 18 wherein the solution of carbohydrates comprises ethylene glycol.

20. The process of claim 13 wherein a portion of the effluent containing glycol product is recycled as solvent for the carbohydrate solution.

* * * * *